(12) United States Patent
Wardlaw

(10) Patent No.: US 6,284,526 B1
(45) Date of Patent: *Sep. 4, 2001

(54) METHOD AND APPARATUS FOR DETERMINING THE SENSITIVITY OF A MICROORGANISM TO A GROWTH ALTERING AGENT

(76) Inventor: Stephen C. Wardlaw, Highrock, Lyme, CT (US) 06371

( * ) Notice: Subject to any disclaimer, the term of this patent is extended or adjusted under 35 U.S.C. 154(b) by 0 days.

This patent is subject to a terminal disclaimer.

(21) Appl. No.: 09/477,932

(22) Filed: Jan. 5, 2000

Related U.S. Application Data

(63) Continuation-in-part of application No. 09/256,451, filed on Feb. 23, 1999, now Pat. No. 6,022,734, and a continuation-in-part of application No. 09/255,681, filed on Feb. 23, 1999, now Pat. No. 6,140,069.
(60) Provisional application No. 60/077,216, filed on Mar. 7, 1998, and provisional application No. 60/077,217, filed on Mar. 7, 1998.

(51) Int. Cl.[7] ............................... C12M 1/16; C12Q 1/18
(52) U.S. Cl. ............................ 435/288.7; 435/287.7; 435/288.3; 435/288.4; 435/32; 435/33
(58) Field of Search .................................. 435/30, 32, 33, 435/287.1, 287.7, 287.8, 287.9, 288.3, 288.4, 288.7, 808, 810, 34, 79, 4, 783.1; 422/56, 61, 82.05, 82.08

(56) References Cited

U.S. PATENT DOCUMENTS

| | | | |
|---|---|---|---|
| 3,925,166 | 12/1975 | Blume | 195/139 |
| 4,054,490 | 10/1977 | Vesterberg | 195/103.5 K |
| 4,204,045 | 5/1980 | Kjellander et al. | 435/301 |
| 4,514,495 | 4/1985 | Schalkowsky et al. | 435/32 |
| 4,778,758 | 10/1988 | Ericsson et al. | 435/32 |
| 4,790,640 | 12/1988 | Nason | 350/534 |
| 4,950,455 | 8/1990 | Smith | 422/56 |
| 5,028,529 | 7/1991 | Ericsson et al. | 435/30 |
| 5,164,301 | 11/1992 | Thompson et al. | 435/29 |
| 5,206,151 | 4/1993 | Robertson | 435/32 |
| 5,246,837 | 9/1993 | Schalkowsky | 435/29 |
| 5,427,959 | 6/1995 | Nishimura et al. | 436/534 |
| 5,501,959 | 3/1996 | Lancaster et al. | 435/32 |
| 5,547,849 | 8/1996 | Baer et al. | 435/7.24 |
| 5,563,043 | 10/1996 | Schalkowsky et al. | 435/32 |
| 5,639,632 | 6/1997 | Ericsson et al. | 435/32 |
| 5,702,684 | 12/1997 | McCoy et al. | 424/10.3 |
| 6,022,734 | * 2/2000 | Wardlaw | . |
| 6,140,069 | * 10/2000 | Wardlaw | . |

FOREIGN PATENT DOCUMENTS 0 635 126 B1    7/1999   (EP) .

* cited by examiner

Primary Examiner—William H. Beisner
(74) Attorney, Agent, or Firm—McCormick, Paulding & Huber LLP

(57) ABSTRACT

A method and an apparatus for determining the concentration at which a growth-altering agent has an appreciable effect on the growth of a target microorganism are provided. The method comprises the steps of (a) providing a microorganism growth medium; (b) providing a sensible reagent, which includes a growth-altering agent mixed with a marker that has a signal with a magnitude proportional to the concentration of the marker; (c) incorporating the sensible reagent into the growth medium, in a manner that creates a gradient of growth-altering agent and marker concentrations within the growth medium; (d) inoculating the growth medium with the target microorganism; (e) incubating the inoculated growth medium for a period of time sufficient for the target microorganism to grow a detectable amount; (f) evaluating growth characteristics of the microorganism in a region containing the growth-altering agent, (g) measuring the magnitude of the marker signal in that region; and (h) determining the concentration of the growth-altering agent using the measured magnitude of the marker signal.

15 Claims, 2 Drawing Sheets

METHOD AND APPARATUS FOR DETERMINING THE SENSITIVITY OF A MICROORGANISM TO A GROWTH ALTERING AGENT

The present application is a continuation-in-part of earlier filed U.S. patent application Ser. No. 09/256,451, filed Feb. 23, 1999, now U.S. Pat. No. 6,022,734, which claims the benefit of U.S. Provisional Application No. 60/077,216, filed Mar. 7, 1998. The present application is also a continuation-in-part of earlier filed U.S. patent application Ser. No. 09/255,681, filed Feb. 23, 1999, now U.S. Pat. No. 6,140,069, which claims the benefit of U.S. Provisional Application No. 60/077,217, filed Mar. 7, 1998.

BACKGROUND OF THE INVENTION

1. Technical Field

The present invention relates to methods and apparatus for determining a microorganism's sensitivity to a growth altering substances in general, and to methods and apparatus for determining the minimum concentration at which a growth altering agent has an appreciable effect on a microorganism in particular.

2. Background Information

Growth-altering agents like antibiotics, antiseptics, drugs, hormones, mutagens, and nutrients can be used to alter, inhibit, or enhance microbial growth. Because the effect of a growth-altering agent is typically a function of its concentration, there is considerable utility in knowing the concentration at which a growth-altering agent will have an appreciable effect on a microorganism. Some existing methods and apparatus for evaluating the effect a growth-altering agent has on a microorganism expose the microorganism to a plurality of discrete concentrations of a growth-altering agent. The Kirby-Bauer test, for example, utilizes a number of disks placed on a layer of growth medium, each of which contains antibiotic in a specific concentration. Bacteria grown on the growth medium form a visible coating, except in the area around those disks having sufficient antibiotic concentration to inhibit bacterial growth. A disadvantage of the Kirby-Bauer test is that there are a number of variables which affect the antibiotic concentration at any given point in the growth medium, and thus do not readily allow for an accurate determination of the minimum inhibitory concentration of the antibiotic.

Another method and apparatus for evaluating the effect a growth-altering agent has on a microorganism is the tube dilution method wherein an equal amount of target microorganism is placed in a plurality of wells (referred to as "tubes") disposed in a platter, and different concentrations of a growth-altering agent are added to each tube. At some concentration of growth-altering agent, there will be an appreciable change in the target microorganism; e.g., its growth will be altered, enhanced, or inhibited. A disadvantage of the tube dilution method is that its accuracy depends on the step size in concentration change between tubes. A small step size yields greater accuracy, but may require an impractical number of tubes and effort. In addition, preparing accurate dilutions is an expensive process that increases in cost with the number of tubes. Hence, increasing the accuracy of this method can also increase the cost and time required.

What are needed are a method and an apparatus for determining the concentration at which a growth-altering agent has an appreciable effect on a target microorganism, and one that can do so accurately in a time effective manner.

DISCLOSURE OF THE INVENTION

It is, therefore, an object of the present invention to provide a method and an apparatus for determining the concentration at which a growth-altering agent has an appreciable effect on a target microorganism.

According to the present invention, a method and an apparatus for determining the concentration at which a growth-altering agent has an appreciable effect on the growth of a target microorganism is provided. The method comprises the steps of (a) providing a microorganism growth medium;

(b) providing a sensible reagent, which includes a growth-altering agent mixed with a marker that has a signal with a magnitude proportional to the concentration of the marker;

(c) incorporating the sensible reagent into the growth medium, in a manner that creates a gradient of growth-altering agent and marker concentrations within the growth medium;

(d) inoculating the growth medium with the target microorganism;

(e) incubating the inoculated growth medium for a period of time sufficient for the target microorganism to grow a detectable amount;

(f) evaluating one or more growth characteristics of the microorganism in a region containing the growth-altering agent;

(g) measuring the magnitude of the marker signal in that region; and (h) determining the concentration of the growth-altering agent using the measured magnitude of the marker signal.

As used herein, the term "growth-altering agent" includes agents that will alter, inhibit, or enhance microbial growth. Examples of growth-altering agents include, but are not limited to, antibiotics, antiseptics, drugs, chemical agents, hormones, mutagens, nutrients, or growth promoting agents. The phrase "growth of a [or the] target microorganism" is defined to include positive or negative growth, mutated growth, and atypical shaped growth.

An advantage of the present invention is that a method for determining the concentration at which a growth-altering agent has an appreciable effect on the growth of a target microorganism is provided that gives accurate results in a minimum amount is of time. The present invention uses a sensible reagent that includes a marker having a signal with a magnitude that is proportional to the concentration of the marker. The concentration of the marker within the reagent is proportional to the concentration of the growth-altering agent. The concentration of the growth-altering agent in a region within the growth medium can therefore be determined by sensing the marker signal in that region. Accordingly, the exact concentration of the growth-altering agent can be determined rather than an approximation, and can be determined without a multitude of time consuming dilution steps.

Another advantage of the present invention is that a cost-effective method for determining the concentration at which a growth-altering agent has an appreciable effect on the growth of a target microorganism is provided. The ability of the present invention method to provide accurate growth-altering agent information obviates the need for expensive multiple dilutions as are required in the tube dilution method. A person of skill in the art will recognize that minimizing expensive medical laboratory time and laboratory assets make the present method likely to be considerably less expensive than presently available methods.

Another advantage of the present invention is that a "user-friendly" apparatus for determining the concentration at which a growth-altering agent has an appreciable effect on the growth of a target microorganism is provided. The present apparatus embodiments facilitate the testing process, minimize the opportunity for sample spillage, and can be readily disposed of after the test. These qualities and others make the present apparatus attractive as a disposable.

These and other objects, features and advantages of the present invention will become apparent in light of the detailed description of the best mode embodiment thereof as illustrated in the accompanying drawings.

DETAILED DESCRIPTION OF THE INVENTION

Figure 1:
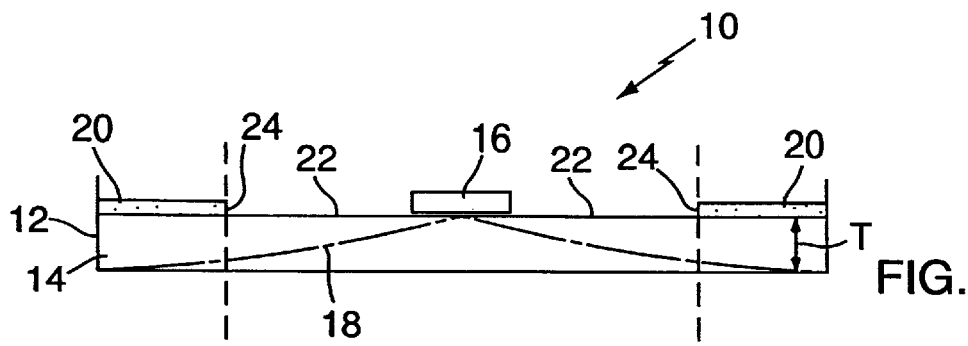
FIG. 1 shows a diagrammatic cross-section of a Kirby-Bauer plate type apparatus to illustrate the present invention method.

The present method for determining the concentration at which a growth-altering agent has an appreciable effect on the growth of a target microorganism includes providing a microorganism growth medium capable of supporting the microorganism, an effective amount of target microorganism, and a sensible reagent. Growth mediums in gel, semi-solid, or permeable-solid form can be used. Dehydrated growth mediums that may be rehydrated during use are particularly favorable because they can be readily stored for extended periods of time. The target microorganism may consist of either first generation microbes taken from a sample of urine, cerebrospinal fluid, body cavity fluid, or a suspension of microbes taken, for example, from a colony grown on another growth medium. The target microorganism may also be acquired from environmental sources such as water, food, or food preparation surfaces.

The sensible reagent includes the growth-altering agent and a marker. In a first embodiment, the sensible reagent contains an accurate quantity of the growth-altering agent mixed with a useful, but imprecisely measured, quantity of marker. In a second embodiment, the growth-altering agent and the marker of the reagent are mixed in known accurate proportion, and the overall quantity of the reagent may vary to suit the application. These reagent embodiments require only one parameter (growth-altering agent quantity or growth-altering agent to marker proportion) to be known accurately, thus minimizing the cost of manufacturing the sensible reagent and consequently the overall method.

The marker may be any material that: 1) has an identifiable signal with a magnitude proportional to the concentration of the marker; 2) has a signal that is distinguishable from other elements within the test sample; 3) has a signal and signal magnitude that are not adversely affected by growth of the target microorganism; 4) does not substantially adversely effect growth of the target microorganism; 5) does not unpredictably or adversely affect the action of the growth-altering agent being evaluated; and 6) one which, if necessary, will co-diffuse with the growth-altering agent in the growth medium during the incubation period in a predictable manner so that the local marker concentration is proportional to the local growth-altering agent concentration. For example, a fluorescent marker having excitation or emission wavelengths outside the range of the excitation or emission wavelengths of the growth medium, and one that does not bind to the growth medium or the target microorganism may be used. The marker and the growth-altering agent preferably diffuse within the growth medium at the same rate, although a similar diffusion rate is not required. A marker and a growth-altering agent having different, but known, diffusion rates may be used alternatively. In another example, an identifiable dye that is absorbed by the growth-altering agent may be used. The magnitude of the marker signal emitted from the dye is proportional to the concentration of growth-altering agent since it is the growth-altering agent that is "carrying" the dye. The terms "proportion" and "proportional" as used within the present specification comprise any relationship that can be mathematically described; e.g., $x:y$, $x:y^2$, $x:1/y$, etc.

The present method includes the further steps of a) incorporating the sensible reagent into the growth medium; b) inoculating the growth medium with the target microorganism; c) incubating the inoculated growth medium; d) evaluating one or more growth characteristics of the microorganism in a region of the growth medium; e) measuring the magnitude of the marker signal in that region; and f) determining the concentration of the growth-altering agent in the region using the magnitude of the marker signal measured in the region. In some applications it may be useful to evaluate the one or more growth characteristics of the microorganism in more than one region of the growth medium. The concentration of the growth-altering agent would be determined in those regions using the same method.

In some applications the present method may include the further step of relating changes in the growth characteristics of the microorganism to the concentration of the growth-altering agent. The manner in which the microorganism growth changes relative to the concentration will depend on the application at hand; e.g., the relationship could be linear, exponential, a step function, etc. The ability of the present method to accurately determine the concentration along a gradient enables the relationship to be determined.

The effects on the organism can be determined in several ways. For example, the growth medium can be examined for areas of contiguous growth where changes in the coverage or density of the growth will be indicative of the effects of the growth-altering agent. A more sensitive method is the examination of individual colonies for changes in characteristics such as growth rate, colony area, colony morphology, etc. Individual organisms or small clusters or microorganisms may also be examined for such changes.

The sensible reagent is incorporated into the growth medium in a manner such that at least one gradient of reagent concentration forms within the growth medium The concentrations of the growth-altering agent and marker at the ends of the gradient are preferably such that the point at which the growth-altering agent has an appreciable effect on the growth of the target microorganism will always fall in between the two ends of the gradient. Incorporation can be accomplished directly, for example by inserting the reagent into the growth medium or by applying the reagent onto a surface of the growth medium. Incorporation can also be accomplished indirectly by applying the reagent onto a substrate and placing the substrate in contact with, or in close proximity to, the growth medium.

The growth medium can be inoculated by any known method acceptable for use with the growth medium and the target microorganism. The number of target microorganism microbes inoculated into the growth medium should be sufficient to provide adequate coverage over the entire area of the growth medium incorporating the reagent. The sufficiency of inoculum concentration will depend on the parameters of the test at hand, including the type growth medium, target microorganism, growth-altering agent etc. The growth medium, incorporated with the sensible reagent and inoculated with the target microorganism, can be incubated under any conditions that are acceptable to the growth medium and the target microorganism.

Because the point(s) at which the growth-altering agent has an appreciable effect on the growth of the target microorganism falls in between the two ends of the gradient, the gradient enables the determination of the effects of the growth-altering agent on the microorganism as a function of the concentration of the growth-altering agent. In most instances, there will be a first section of the growth medium having no appreciable effects from the growth-altering agent, a second section of the growth medium having appreciable effects from the growth-altering agent on one or more growth characteristics, and a boundary region located between the first and second sections. The extent of the boundary region will depend on circumstances at hand including the type growth-altering agent, the microorganism, the slope of the concentration gradient, etc. Depending upon the growth-altering agent and the microorganism, the changes across the boundary region may be mathematically related to the concentration of the growth-altering agent. In the case of a growth-altering agent that promotes growth, for example, an exact growth concentration curve producible from such a mathematical relationship could help choose the optimal cost/benefit ratio for the addition of such agents into a commercial process.

If the growth-altering agent is an inhibiting agent, for example, the boundary region will define the border between a first section having substantially uninhibited development (where the concentration of the inhibiting agent was too low and therefore did not have an appreciable effect on the microorganism) and a second section having substantially inhibited development (where the concentration of the inhibiting agent was great enough to have an appreciable effect on the microorganism). The point on the gradient at which the boundary region falls is the minimum concentration at which the growth-altering agent will have an appreciable effect on the growth of the microorganism. If on the other hand the growth-altering agent is a nutrient, a first section (having an effective concentration of nutrient) might have appreciably advanced rate of development relative to a second section (having an ineffective concentration of nutrient).

Another example of characteristic growth differences is an appreciable difference in the atypical forms of the microorganism. If the growth-altering agent can cause the microorganism to produce atypical forms of the microorganism, there will be a first section having substantially normal forms of the microorganism (where the concentration of the growth-altering agent was too low and therefore did not have an appreciable effect on the microorganism) and a second section having a statistically substantial population of atypical forms of the microorganism (where the concentration of the growth-altering agent was great enough to have an appreciable effect on the microorganism).

The effects of the growth-altering agent on the microorganism and the position of the boundary region are usually determined by optical means, for example by changes in the optical density of the coat of microorganisms on the medium. In some instances, a second method for determining the effects of the growth-altering agent and the position of the boundary region may be used that involves a marker (which may be the same as, or independent of, the marker contained within the reagent) that interacts with, including but not limited to being metabolized by, the growing microorganism to produce a sensible product. The sensible product, which is present with the target microorganism growth, is sensed to establish the boundary. A third method for determining the effects of the growth-altering agent and the position of the boundary region includes evaluating the light scattering characteristics within the section(s) bearing target microorganism growth versus the light scattering characteristics in the section(s) bearing substantially no target microorganism growth. In all three methods, once the boundary region is determined, the signal from the marker within the reagent can be sensed and its magnitude measured. If individual colonies or organisms in those sections of the growth medium are to be evaluated, they may readily be viewed or photographed using a magnifier or a microscope.

The marker mixed with the growth-altering agent in the sensible reagent provides the quantitative information in all sections of the growth medium, including the boundary region that enables the concentration of the growth-altering agent to be calculated. Specifically, the magnitude of the marker signal in the boundary region is proportional to the marker concentration in the boundary region, and the concentration of the growth-altering agent can be determined using the known proportional relationship between the concentrations of marker and growth-altering agent. The exact method for determining the growth-altering agent concentration will depend on the physical embodiments of the growth medium, how the sensible reagent is distributed, the proportional relationship between the marker and the growth-altering agent within the reagent, etc. The following examples illustrate how the growth-altering agent concentration may be calculated using the present invention method.

EXAMPLE I

Figure 2:
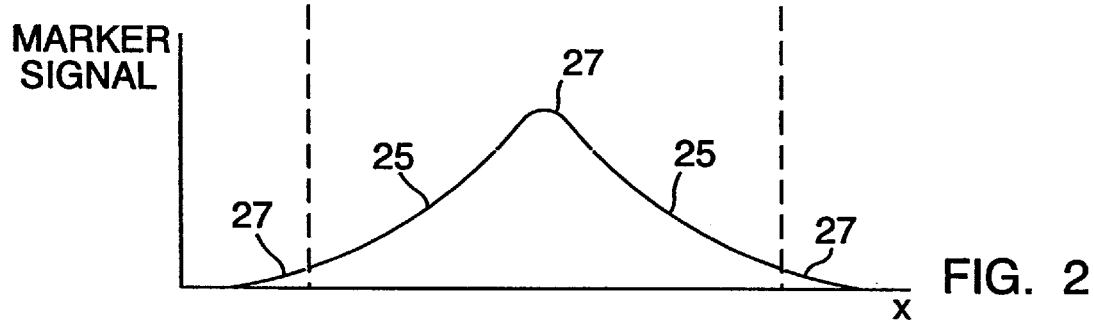
FIG. 2 is a graph depicting marker signal magnitude as a function of linear distance, associated with the Kirby-Bauer type apparatus shown in FIG. 1.

Referring to FIGS. 1 and 2, in a first example the present invention method uses a Kirby-Bauer type apparatus 10 (shown in diagrammatic cross-section) which includes a plate 12, a layer of microorganism growth medium 14 of uniform thickness "T" inoculated with a target microorganism, and a disk 16. The sensible reagent (with an accurately known quantity of growth-altering agent mixed with an imprecisely measured quantity of fluorescent marker) is applied to the disk 16 and the disk is placed in contact with the growth medium 14. The sensible reagent diffuses into the growth medium 14, creating a concentration gradient 18 as it travels radially (shown diagrammatically in FIG. 1). The inoculated growth medium 14 is incubated and a section 20 having detectable microorganism growth develops contiguous with a section 22 having no detectable microorganism growth.

Referring to FIGS. 1 and 2, the plate is placed in a commercially available scanning fluorometer (not shown) adjusted to sense the fluorescent signal characteristic of the marker. The fluorometer generates a curve 25 (FIG. 2) representing signal magnitude as a function of radial distance across the plate. Marker signal magnitude is a function of the marker concentration in a given volume (V), and is determined by sensing an area (A) of the growth medium which has a uniform thickness (T; V=A*T). The marker signal magnitude in the boundary region 24 between the sections 20, 22, for example, is given as the signal magnitude measured within a volume (V) of growth medium located in the boundary region 24. As stated earlier, the position of the boundary region 24 between the sections 20, 22 may be determined optically, or by other means. In the growth medium 14 below the disk 16 and the section 20 of growth medium having detectable target microorganism growth, the signal from the marker may be obscured by interference. The total signal magnitude from the marker can be determined by estimating the marker signal magnitude in the obscured regions with a curve fitting mathematical analysis. For illustrative purposes, FIG. 2 shows an example of a mathematically fit curve 27 in the obscured regions. The total signal magnitude from the marker is subsequently determined by integrating the area under the curve. As described above, the marker signal is scanned in a linear manner across the center of the test area. Since the sensible reagent actually diffuses radially in the round growth medium, it may be necessary to adjust the signal integration to reflect the radial diffusion of the reagent. The signal integration adjustment may be avoided, however, by scanning the entire area containing the radial diffusion of reagent.

The concentration of marker in the given volume (V) in the boundary region 24 can be expressed as the ratio of the magnitude of the marker signal in the boundary region 24 (sensed from volume V) over the total magnitude of the marker signal sensed within the total volume of the growth medium 14. The concentration of marker in the boundary region 24, in turn, is related to the concentration of the growth-altering agent in the boundary region 24 (in the same volume V), by the ratio of diffusion rates of the marker and growth-altering agent. If the diffusion rates are equal, the growth-altering agent concentration in the boundary region can be determined as follows:

$$\frac{[(\text{mag. of signal})/(V)]_b}{[(\text{mag. of signal})/(\text{total volume})]_{tot}} = \frac{[(\text{am't of growth-altering agent})/(V)]_b}{[(\text{am't of growth-altering agent})/(\text{total volume})]_{tot}}$$

which can be rearranged to solve for the unknown growth-altering agent concentration in the boundary region 24:

$$\frac{[(\text{mag. of signal})/(V)]_b * [(\text{am't of growth-altering agent})/(\text{total volume})]_{tot}}{[(\text{mag. of signal})/(\text{total volume})]_{tot}} = [(\text{am't of growth-altering agent})/(V)]_b$$

If the diffusion rates of the growth-altering agent and marker differ, a correction factor representing the mathematical relationship between the two diffusion rates is used to correct for the difference. In addition, the above expressions require that the quantity of growth-altering agent in the total volume of growth medium 14 be accurately known. If all the sensible reagent (containing an accurately known quantity of growth-altering agent mixed with an imprecisely measured quantity of fluorescent marker) is incorporated into the growth medium, then the quantity of growth-altering agent is ascertainable from the reagent. Other methods of accurately determining the quantity of growth-altering agent within the total volume of growth medium 14 may be used alternatively.

EXAMPLE II

Figure 3:
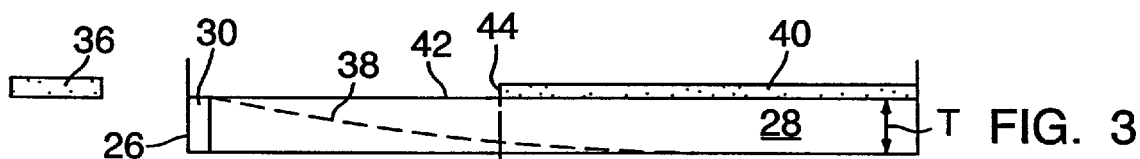
FIG. 3 shows a diagrammatic cross-section of a trough containing a microorganism growth medium to illustrate the present invention method.
Figure 4:
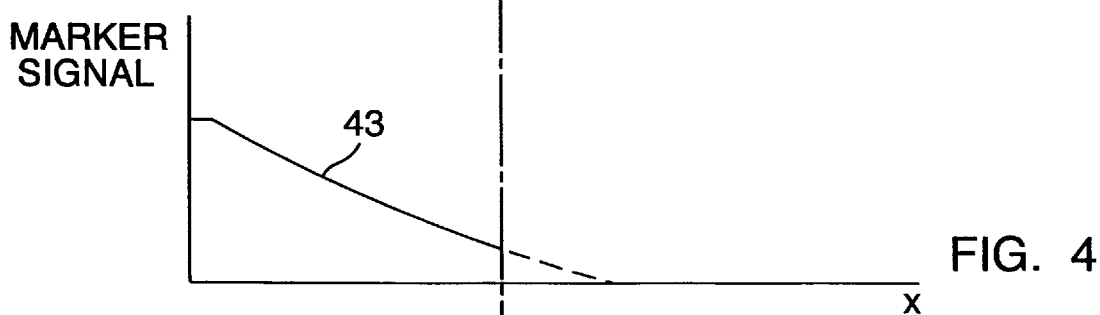
FIG. 4 is a graph depicting marker signal magnitude as a function of linear distance, associated with the apparatus shown in FIG. 3.
Figure 5:
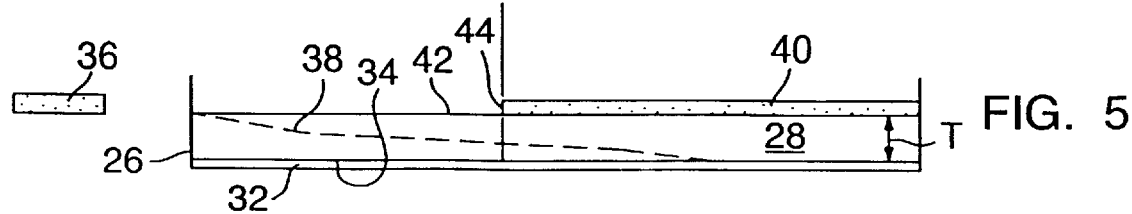
FIG. 5 shows the diagrammatic cross-section shown in FIG. 3, further including sensible reagent applied to a substrate.

Referring to FIGS. 3–5, a trough 26 contains a layer of growth medium 28 of known uniform thickness "T" inoculated with a target microorganism. FIG. 3 illustrates an embodiment where a quantity of sensible reagent containing a known accurate concentration ratio of growth-altering agent and marker is applied to a surface 30 of the growth medium 28 located at one end of the trough 26. FIG. 5 illustrates an alternative embodiment where a quantity of sensible reagent containing a known accurate concentration ratio of growth-altering agent and marker is applied to a substrate 32 placed in contact with a surface 34 of the growth medium 28. In both embodiments, the ratio of growth-altering agent to marker initial concentrations is chosen to ensure that the growth-altering agent and the marker will diffuse into the growth medium 28 sufficiently enough so as to provide a readily detectable quantity of marker at the probable boundary region. The ratio of initial concentrations is expressed as the constant "$k_1$":

$$k_1 = (\text{growth-altering agent concentration})_{initial}/(\text{marker concentration})_{initial}$$

An accurate value representing the ratio of growth-altering agent to marker initial concentrations is determined at the time the sensible reagent is manufactured. A reference pad 36, independent of the layer of growth medium 28, is provided containing a known amount of marker that emits a known magnitude of fluorescent signal. The marker contained within the reference pad 36 can be different from that used within the reagent. If the markers are different, however, or if the response of the marker within the reference pad 36 differs from the response of the marker in the growth medium 28, the concentration to signal magnitude ratio of each marker must be known.

The sensible reagent diffuses into the growth medium 28, creating a gradient 38 of decreasing concentration as it travels laterally (shown diagrammatically in FIGS. 3 and 5). The inoculated growth medium 28 is incubated and a section 40 having detectable microorganism growth develops contiguous with a section 42 having no detectable microorganism growth. A commercially available scanning fluorometer (not shown) adjusted to sense the fluorescent signal characteristic of the marker is used to measure the magnitude of the marker signal emitted from a given volume (V) located in the boundary region 44 between the sections 40, 42, where the volume (V) is defined as an area (A) of inoculated growth medium scanned, having a uniform thickness (T; V =A*T). As stated earlier, the position of the boundary region 44 between the sections 40, 42 may be determined optically, or by other means. The fluorometer generates a curve 43 (FIG. 4) representing signal magnitude as a function of lateral distance across the trough 26.

The concentration of the growth-altering agent in the boundary region 44 can be calculated by first determining the marker concentration in a given volume (V) in the boundary region 44 using the following relationship:

$$\frac{[\text{am't of marker}]_{ref}}{[\text{mag. of signal}]_{ref}} = \frac{[(\text{am't of marker})/(V)]_b}{[(\text{mag. of signal})/(V)]_b}$$

which can be rearranged to solve for the unknown marker concentration since the marker signal in the boundary region 44 is known:

$$\frac{[\text{am't of marker}]_{ref} * [(\text{mag. of signal})/(V)]_b}{[\text{mag. of signal}]_{ref}} = [(\text{am't of marker})/(V)]_b$$

Once the marker concentration in the boundary region 44 is determined, the growth-altering agent concentration in the boundary region 44 can be determined by multiplying the ratio ($k_1$) of growth-altering agent and marker initial concentrations times the marker concentration in the boundary region 44, provided the growth-altering agent and the marker within the sensible reagent have equal diffusion rates:

$k_1*[(\text{am't of marker})/(V)]_b$=Growth-Altering Agent Concentration in the Boundary Region If the diffusion rates of the growth-altering agent and marker differ, a correction factor representing the mathematical relationship between the two diffusion rates is used to correct for the difference.

Figure 6:
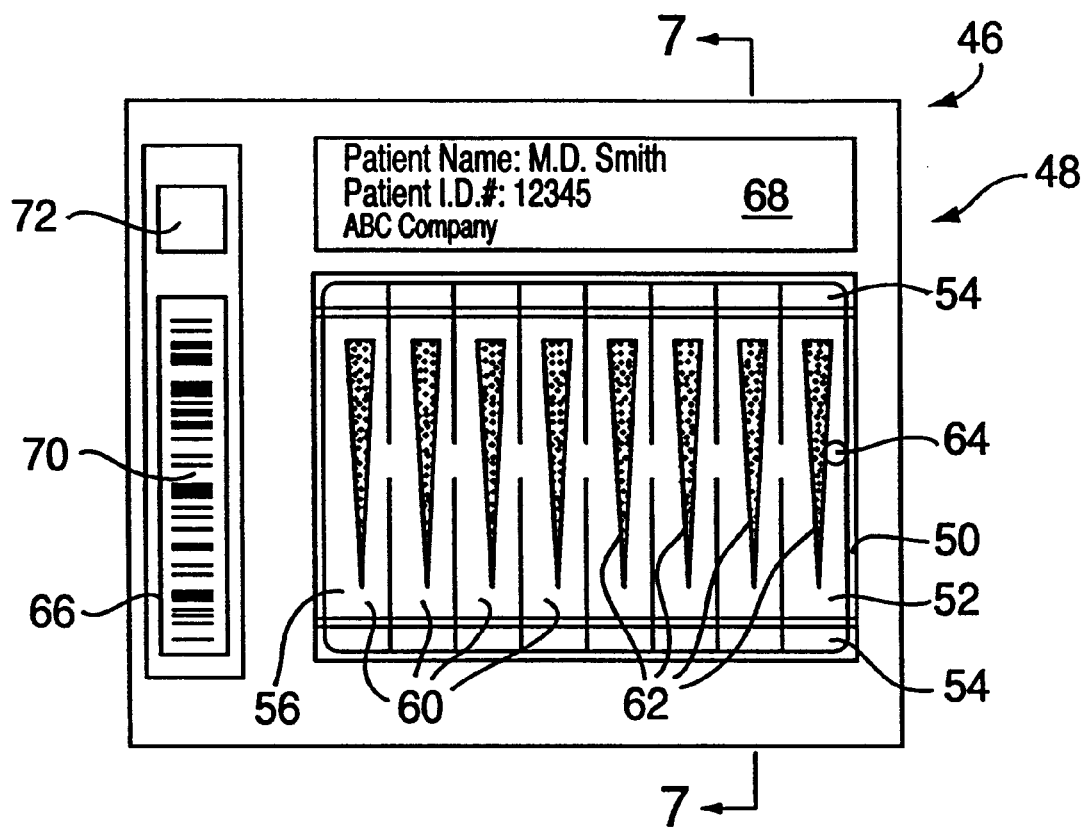
FIG. 6 is a diagrammatic view of a present invention apparatus embodiment.
Figure 7:
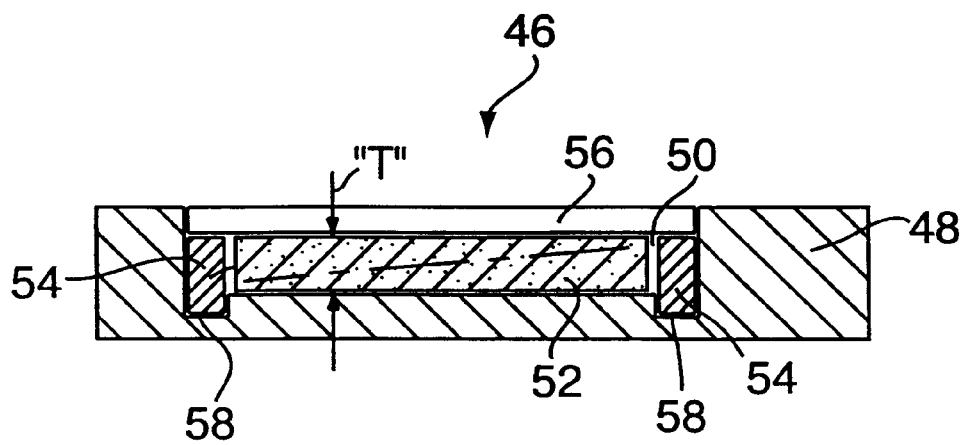
FIG. 7 is a cross-sectional view of the apparatus shown in FIG. 6.

Referring to FIGS. 6 and 7, a preferred apparatus 46 for use in determining the concentration at which a growth-altering agent has an appreciable effect on the growth of a target microorganism includes a body 48 having a well 50, sensible reagent incorporated into a sheet of the growth medium 52, a pair of absorbent strips 54, and a transparent well cap 56. The well 50 includes a pair of channels 58 extending between walls of the well 50. The growth medium 52 is disposed in the well 50 and an absorbent strip 54 is placed in each channel 58. The growth medium 52 shown in FIG. 7 contains a number of distinct sections 60, each incorporating a gradient strip 62 of reagent. In instances where there is utility in evaluating a plurality of different growth-altering agents, each gradient strip 62 of reagent may contain a different growth-altering agent. The transparent well cap 56 attaches to the body 48 above the well 50 to protect and maintain the growth medium 52 and absorbent strips 54 inside the well 50. The apparatus body 48 may alternatively include a plurality of wells 50, each similar to that described above. The apparatus further includes a port 64 through which a target microorganism solution can be distributed to the growth medium 52.

The apparatus 46 further includes a machine-readable information label 66 and a user readable information label 68. The machine-readable information label 66 includes a data block 70 containing pertinent information such as the test to be performed, calibration constants, patient identification, or the like, in a machine-readable format such as a bar code or magnetic strip. Depending upon the analysis application, the machine-readable label 66 may directly contain all of the information necessary to enable an analytical device to perform the analysis at hand. In other instances, the machine-readable label 66 may instruct the analytical device to access data files contained within the analytical device or remotely accessed by the analytical device. Hence, it can be said that the label 66 directly or indirectly contains the information necessary to enable an analytical device to perform the analysis at hand. The machine-readable information label 66 may also include a reference pad 72 containing a known amount of a sensible marker for use in analyzing the reagent marker signal within the growth medium. The user-readable information label 68 includes information that enables the apparatus 46 to be identified by the user without machine assistance.

Although this invention has been shown and described with respect to the detailed embodiments thereof, it will be understood by those skilled in the art that various changes in form and detail thereof may be made without departing from the spirit and the scope of the invention.

What is claimed is:

1. A method for determining a concentration at which a growth-altering agent has an appreciable effect on the growth of a microorganism, comprising the steps of:

(a) providing a microorganism growth medium;

(b) providing a sensible reagent, which includes a growth-altering agent mixed with a first marker, said first marker having a first signal with a magnitude proportional to said first marker's concentration;

(c) incorporating said reagent into said growth medium, in a manner that creates a gradient of concentrations of said growth-altering agent and said first marker within said growth medium;

(d) inoculating said growth medium with said target microorganism;

(e) incubating said inoculated growth medium for a period of time sufficient for said target microorganism to grow a detectable amount;

(f) evaluating said growth of said microorganism in a region containing said growth-altering agent;

(g) measuring said magnitude of said first signal in said region; and (h) determining said concentration of said growth-altering agent in said region using said measured magnitude of said first signal.

2. The method of claim 1, wherein said reagent is incorporated into said growth medium by applying said reagent onto a surface of said growth medium.

3. The method of claim 1, wherein said incorporating step includes applying said sensible reagent onto a substrate and placing said substrate in contact with, or in close proximity to, said growth medium.

4. The method of claim 1, wherein said step of providing said sensible reagent further comprises:

providing said growth-altering agent in an accurate known quantity mixed with a useful quantity of said marker.

5. The method of claim 1, wherein said step of providing said sensible reagent further comprises:

providing said growth-altering agent and said first marker in known accurate proportion, wherein said accurate proportion may be mathematically represented as a ratio of an initial growth-altering agent concentration over an initial marker concentration.

6. The method of claim 1, wherein said region is disposed between a first section of said growth medium having no appreciable effects from said growth-altering agent and a second section of said growth medium having appreciable effects from said growth-altering agent.

7. The method of claim 6, further comprising the steps of:

sensing said growth medium for differences in light scattering characteristics; and determining said region using said light scattering characteristics.

8. The method of claim 1, further comprising the step of:

relating one or more changes in said growth of said microorganism to said concentration of said growth-altering agent.

9. The method of claim 8, wherein said first signal is measured in a plurality of regions along said gradient.

10. A method for determining the minimum concentration at which a growth-altering agent has an appreciable effect on the growth of a target microorganism, comprising the steps of:

(a) providing a microorganism growth medium;

(b) providing a sensible reagent, which includes a growth-altering agent mixed with a marker, said marker having a signal with a magnitude which is proportional to said marker's concentration;

(c) incorporating said reagent into said growth medium, in a manner that creates a gradient of concentrations of said growth-altering agent and said marker within said growth medium;

(d) inoculating said growth medium with said target microorganism;

(e) incubating said inoculated growth medium for a period of time sufficient for said target microorganism to grow a detectable amount;

(f) evaluating said growth medium for sections of said growth medium having appreciable differences in microorganism growth characteristics, said sections separated from one another by a boundary region;

(g) measuring said magnitude of said marker signal in said boundary region; and (h) calculating said concentration of said growth-altering agent using said measured magnitude of said marker signal.

11. A method for determining the concentration at which a growth-altering agent has an appreciable effect on the growth of a target microorganism, comprising the steps of:

(a) providing a microorganism growth medium having a sensible reagent that includes a growth-altering agent mixed with a marker, said marker having a signal with a magnitude that is proportional to said marker's concentration;

(b) innoculating said growth medium with said target microorganism;

(c) incubating said innoculated growth medium for a period of time sufficient for said target microorganism to grow a detectable amount;

(d) determining a boundary region between a pair of contiguous sections of said growth medium having differences in microorganism growth;

(e) sensing said marker signal in said boundary region; and (f) calculating a concentration of said growth-altering agent using said sensed marker signal.

12. An apparatus for determining a concentration at which a growth-altering agent has an appreciable effect on the growth of a target microorganism, comprising:

a sheet of microorganism growth medium; and a sensible reagent that includes a growth-altering agent and a marker, said marker having a signal with a magnitude proportional to said marker's concentration;

wherein said reagent is incorporated into said sheet of growth medium in a manner that creates a gradient of concentrations of said growth-altering agent and said marker within said growth medium.

13. The apparatus of claim 12, wherein said sensible reagent includes said growth-altering agent in an accurate known quantity mixed with a useful quantity of said marker.

14. The apparatus of claim 12, wherein said sensible reagent includes said growth-altering agent and said first marker in known accurate proportion, and said accurate proportion may be mathematically represented as a ratio of an initial concentrations.

15. The apparatus of claim 12, further comprising:

a sensor for sensing for said marker signal; and means for detecting growth of said target microorganism;

wherein said sensor is operable to sense for said marker signal at a boundary detected contiguous with said target microorganism growth.

* * * * *

UNITED STATES PATENT AND TRADEMARK OFFICE
CERTIFICATE OF CORRECTION

PATENT NO.     : 6,284,526 B1
DATED          : September 4, 2001
INVENTOR(S)    : Stephen C. Wardlaw It is certified that error appears in the above-identified patent and that said Letters Patent is hereby corrected as shown below:

<u>Title page,</u>
Item [73], add the following Assignees
--     Robert A. Levine
       Guilford, CT. (US)

Wardlaw Partners, LP
       Lyme, CT (US) --

Signed and Sealed this

Tenth Day of September, 2002

Attest:

Attesting Officer

JAMES E. ROGAN
*Director of the United States Patent and Trademark Office*